United States Patent [19]

Englert et al.

[11] Patent Number: 4,766,241
[45] Date of Patent: Aug. 23, 1988

[54] 2-AMINOMETHYL-6-SULFAMOYLPHENOL DERIVATIVES WITH SALIDIURETIC ACTIVITIES

[75] Inventors: Heinrich C. Englert, Hofheim am Taunus; Dieter Mania, Kelkheim Taunus; Roman Muschaweck, Frankfurt am Main; Max Hropot, Flörsheim am Main, all of Fed. Rep. of Germany

[73] Assignee: Hoechst Aktiengesellschaft, Fed. Rep. of Germany

[21] Appl. No.: 102,793

[22] Filed: Sep. 23, 1987

Related U.S. Application Data

[60] Continuation of Ser. No. 868,522, May 30, 1986, abandoned, which is a division of Ser. No. 751,995, Jul. 3, 1985, Pat. No. 4,607,030, which is a continuation of Ser. No. 472,005, Mar. 4, 1983, abandoned.

[30] Foreign Application Priority Data

Mar. 6, 1982 [DE] Fed. Rep. of Germany ....... 3208189

[51] Int. Cl.$^4$ .......................................... C07C 143/80
[52] U.S. Cl. ..................................................... 564/89
[58] Field of Search .......................................... 564/89

[56] References Cited

FOREIGN PATENT DOCUMENTS 2246403 3/1973 Fed. Rep. of Germany ........ 564/89
2461601 7/1976 Fed. Rep. of Germany .
2658766 7/1978 Fed. Rep. of Germany .

OTHER PUBLICATIONS

Stokker, et al., J. Med. Chem., 1980, 23, 1414–1427.
Patent Abstracts of Japan, vol. 3, No. 87, 1979; p. 41, C 53 8 JP A– 54 63048.

Primary Examiner—Nicky Chan
Attorney, Agent, or Firm—Finnegan, Henderson Farabow, Garrett and Dunner

[57] ABSTRACT

The invention relates to 2-aminomethylphenols of the formula I

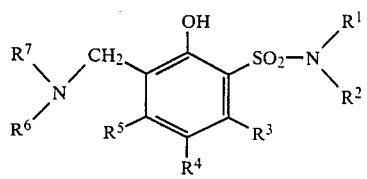

in which $R^1$ and $R^2$ represent hydrogen, alkyl, alkenyl, alkynyl, cycloalkyl or benzyl which is optionally substituted by alkyl, alkoxy or halogen, $R^3$ and $R^5$ denote hydrogen, halogen, alkyl or alkoxy, $R^4$ denotes halogen, alkyl or cycloalkyl and $R^6$ and $R^7$ represent hydrogen or alkyl, it being possible for the radicals $R^1$ and $R^2$, $R^6$ $R^7$ and/or two of the radicals $R^3$, $R^4$ and $R^5$ to form an alkylene chain which is optionally substituted by methyl groups and which, in the case of the radicals $R^1$, $R^2$, $R^6$ and $R^7$, can also be interrupted by oxygen atoms, sulfur atoms and/or imino groups, and to physiologically acceptable salts thereof, a process for their preparation, and their use and to pharmaceutical formulations based on these compounds.

1 Claim, No Drawings

2-AMINOMETHYL-6-SULFAMOYLPHENOL DERIVATIVES WITH SALIDIURETIC ACTIVITIES

This application is a continuation of application Ser. No. 868,522, filed May 30, 1986, now abandoned, which was a divisional of application Ser. No. 751,995, filed July 3, 1985 (now U.S. Pat. No. 4,607,030), which was a continuation of application Ser. No. 472,005, filed Mar. 4, 1983, now abandoned.

The invention relates to 2-aminomethyl-6-sulfamoylphenols of the formula I

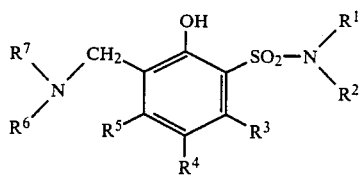

in which
- $R^1$ and $R^2$ are identical or different and represent hydrogen, alkyl having 1 to 8 carbon atoms, alkenyl having 2 to 8 carbon atoms, alkynyl having 2 to 8 carbon atoms, cycloalkyl having 3 to 12 carbon atoms and up to 8 ring members or benzyl which is optionally substituted by alkyl having 1 to 4 carbon atoms, alkoxy having 1 to 4 carbon atoms or halogen,
- $R^3$ and $R^5$ are identical or different and denote hydrogen, halogen, alkyl having 1 or 2 carbon atoms or alkoxy having 1 or 2 carbon atoms,
- $R^4$ denotes halogen, alkyl having 1 to 12 carbon atoms or cycloalkyl having 3 to 12 carbon atoms and up to 8 ring members, and
- $R^6$ and $R^7$ are identical or different and represent hydrogen or alkyl having 1 to 4 carbon atoms, it being possible for the radicals $R^1$ and $R^2$, $R^6$ and $R^7$ and/or two of the radicals $R^3$, $R^4$ and $R^5$ to form a $-[CH_2]_m-$ chain in which m is 3 to 6 and which is optionally substituted by 1 or 2 methyl groups and which, in the case of the radicals $R^1$, $R^2$, $R^6$ and $R^7$, can also be interrupted by 1 or 2 oxygen atoms, sulfur atoms and/or imino groups, and to physiologically acceptable salts thereof.

If one of the cycloalkyl groups defined above has a number of carbon atoms which exceeds the number of members in the ring, it is to be understood as meaning a cycloalkyl group which is substituted by one or more alkyl groups or an optionally alkyl-substituted cycloalkylalkyl group.

2-Aminomethylphenols substituted in the 6-position are already known from J. med. Chem. 23 [1980], pages 1414–1427. The corresponding 4-alkyl-6-halogeno derivatives have in some cases salidiuretic properties of the type and strength such as are shown by diuretics having a short and intensive action, such as, for example, furosemide.

In most cases, replacing the halogen atoms in the 6-position by other substituents causes a weakening or even the loss of the salidiuretic activity.

It was therefore extremely surprising that the compounds, according to the invention, of the formula I exert, in dogs or rats, a salidiuretic action which can attain the order of magnitude of the activity of the halogen derivatives described above, in particular that of the iodine compound. They differ, however, in an advantageous manner in that they exhibit a substantially lower acute toxicity, as can be demonstrated in rats.

Preferred compounds of the formula I are those wherein $R^1$ and $R^2$ are identical or different and represent hydrogen, alkyl having 1 to 4 carbon atoms, alkenyl or alkynyl having 2 to 4 carbon atoms and benzyl which is optionally substituted by methyl, methoxy or halogen, $R^3$ and $R^5$ have the meaning mentioned above, $R^4$ is halogen, alkyl having 1 to 8 carbon atoms, cycloalkyl having 3 to 10 carbon atoms and up to 7 ring members, and $R^6$ and $R^7$ are identical or different and denote hydrogen or alkyl having 1 to 2 carbon atoms, it being possible for the radicals $R^1$ and $R^2$, $R^6$ and $R^7$ and/or two of the radicals $R^3$, $R^4$ and $R^5$ to form a polymethylene chain defined above.

Compounds, according to the invention, of the general formula I which are particularly suitable are those in which
- $R^1$ and $R^2$ denote identical or different radicals, namely hydrogen, methyl or ethyl, or both together denote $-[CH_2]_4-$,
- $R^3$ and $R^5$ represent hydrogen,
- $R^4$ denotes isopropyl, tert.-butyl, n-butyl, n-propyl, sec.-butyl, tert.-amyl or cyclopentyl and
- $R^6$ and $R^7$ denote hydrogen, particularly preferred compounds being those in which $R^1$ and $R^2$ denote hydrogen or together denote $-[CH_2]_4-$,
- $R^3$ and $R^5$ denote hydrogen,
- $R^4$ denotes isopropyl, tert.-butyl or sec.-butyl and
- $R^6$ and $R^7$ denote hydrogen.

The invention also relates to a process for the preparation of compounds of the formula I which comprises (a) reacting a phenol of the formula II

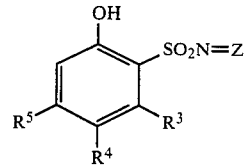

in which the radicals $R^3$ to $R^5$ have the meanings mentioned above and Z represents either the two radicals $R^1$ and $R^2$, which have the meanings mentioned above, with the exception of that of hydrogen, or represents a protective group of the formula III

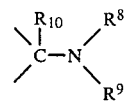

in which the radicals $R^{10}$ denote hydrogen or alkyl having 1 to 4 carbon atoms and $R^8$ and $R^9$ denote alkyl having 1 to 4 carbon atoms, with an N-hydroxymethylcarboxamide of the formula IV

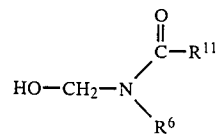

in which $R^6$ has the meaning mentioned above and $R^{11}$ represents hydrogen, alkyl having 1 to 4 carbon atoms, halogenoalkyl having 1–4 carbon atoms or aryl having 6 to 10 carbon atoms, or in which $R_5$ and the radical $COR^{11}$ together represents the o-phthaloyl radical, to give compounds of the formula V

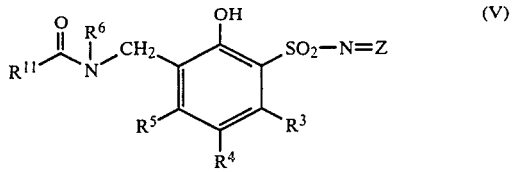

and splitting off, by hydrolysis, the radical $R^{11}$—C— and, if required, the protective group Z, to give compounds of the general formula I, (b) reacting a phenol of the formula II in which the radicals $R^3$ to $R^5$ and also Z have the meanings mentioned above, with an amine of the formula VI

in which $R^7$ and $R^6$ have the meaning mentioned above, with the exception of that of hydrogen, in the presence of formaldehyde and, if appropriate, splitting off the sulfonamide protective group Z by hydrolysis, (c) chlorosulfonating phenols of the formula VII

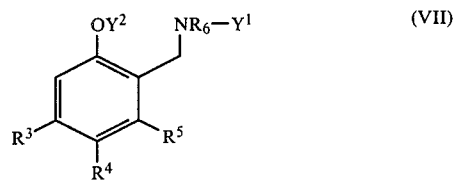

in which $R^3$ to $R^6$ have the meanings mentioned above and $Y^1$ represents the radical $R^{11}$—CO—, $R^{11}$ having the meaning mentioned above and $Y^2$ denoting either hydrogen or $Y^1$, to give compounds of the formula IX

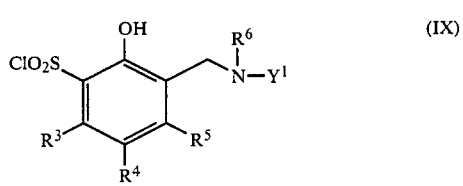

and reacting the latter with amines of the formula X

in which $R^1$ and $R^2$ have the meanings mentioned above, to give compounds of the general formula XI

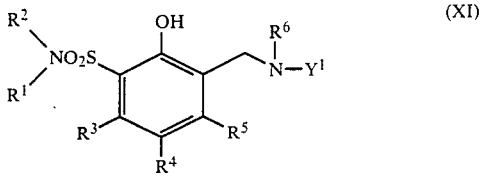

and splitting off the radical $Y^1$ from these by hydrolysis, or (d) reacting compounds of the general formula XVIII

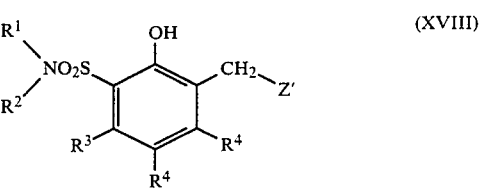

in which $R^1$ to $R^5$ have the meanings mentioned above, it being also possible, however for $R^1$ and $R^2$ together to represent the sulfonamide protective group Z mentioned in process variant a, and Z' representing a leaving group, such as, for example, halogen, tosylate, dimethylamine or trimethylammonium, with amines of the general formula H—N=Y' in which Y' either represents the radicals $R^6$ or $R^7$ defined above or represents one of the radicals $R^6$ or $R^7$ and an amine protective group, such as, for instance, the benzyl radical or the acyl radical CO—$R^{11}$ in which $R^{11}$ has the meaning stated under process variant a, or Y' by itself represents an amine protective group, such as, for example, the diazo radical or the phthaloyl radical, to give the compounds of the general formula XIX

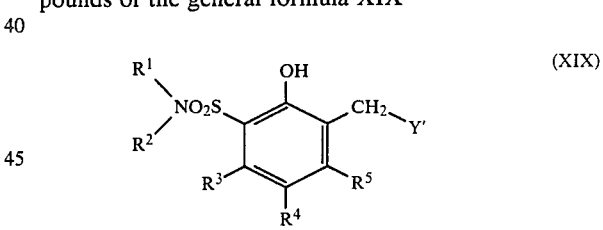

and splitting off from the latter, if appropriate, the amine protective group and/or the sulfonamide protective group by hydrolysis or hydrogenolysis.

The invention also relates to compounds of the general formula II

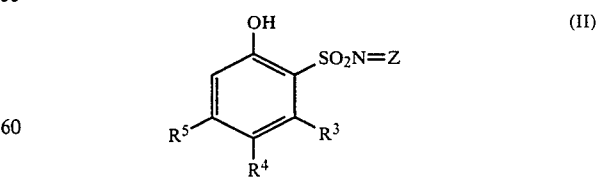

in which $R^3$ to $R^5$ have the meanings indicated above and Z either represents the radicals $R^1$ and $R^2$ defined above or represents the sulfonamide protective group defined in accordance with process variant a.

The elimination of the radical and, if appropriate, of the protective group Z in compounds of the general formula V according to process variant a is generally carried out by means of a base or an acid in the presence of water. If the elimination is carried out under acid conditions, it is preferable to use a strong mineral acid, such as hydrochloric acid, hydrobromic acid or hydriodic acid or sulfuric acid. If, on the other hand, saponification is carried out under alkaline conditions, it is advantageous to use strong inorganic bases, such as alkali metal or alkaline earth metal bases, such as, for instance, sodium hydroxide or barium hydroxide, but it is also possible to use strong organic bases, such as quaternary ammonium hydroxides, for example tetraethylammonium hydroxide. The solvent used can be virtually any solvent which is inert towards the reactants, such as, for example, alkanols, preferably ethanol, or, if hydrolysis is carried out under acid conditions, alkanoic acids, such as, for example, acetic acid. At least one equivalent of water per saponifiable group must be added to the reaction mixture, but in most cases a greater excess is employed or water on its own is used as the solvent, which is particularly advantageous for alkaline saponifications.

The reaction temperature can be between 20° and 150° C.; the reaction is advantageously carried out at the reflux temperature of the solvent. In these reactions the elimination of the sulfonamide protective group is generally effected considerably more rapidly than the elimination of the radical

After acid saponification, the reaction product is in most cases produced in a crystalline form as the acid addition salt, immediately or after removing the solvent by evaporation.

In the case of alkaline saponification of the compounds, after neutralizing excess base, the free benzylamine I is generally formed immediately.

The preparation of the compounds of the formula V is effected in a manner known per se by subjecting the phenols of the general formula II to an acid-catalyzed reaction of the Tscherniac-Einhorn type with N-hydroxymethylcarboxamides of the general formula IV, preferably with 2-halogeno-N-hydroxymethylacetamides, such as, for example, 2-chloro-N-hydroxymethylacetamide. Suitable catalyst acids are, above all, strong mineral acids, such as, for instance, sulfuric acid or hydrochloric acid. Any solvent customary for Tscherniac-Einhorn reactions can be used, alkanoic acids, such as acetic acid or propionic acid, are particularly suitable, but excess mineral acid, such as, for example, pure concentrated sulfuric acid, can also be advantageous as the solvent. The reactions are carried out between 0° and 100° C., advantageously in the range from 0° to 30° C. in order to avoid by-products.

In particular, it has been found that, if the reaction time, which can be between 10 minutes and a few hours, depending on the compound and the reaction temperature, is precisely adhered to, amidoalkylation reactions of this type can still be carried out successfully even when using more rigorous reaction conditions (such as, for instance, concentrated sulfuric acid as the solvent), which in certain circumstances prove necessary for a rapid and complete reaction. Likely side reactions, such as, for instance, dealkylation, in particular the elimination of the tert.-butyl group (for example $R^4$=tert.-butyl in the general formula II or V), can be reduced to a minimum by precisely controlled reaction conditions.

The reaction products are isolated most advantageously by adding to the reaction mixture a non-solvent, such as, for instance, water; the product is then, as a rule, obtained in a crystalline state immediately and can be processed further after recrystallization from a suitable solvent or, in many cases, without further purification.

An example of a method of preparing the phenols which are used as starting compounds for the process variants a and b is subjecting to ether-splitting anisoles of the general formula XII

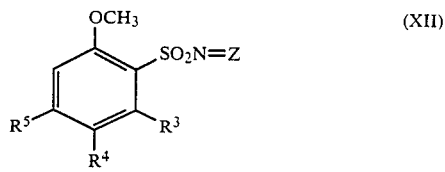

or other alkyl phenol ethers carrying an $O-(C_2-C_6)$-alkyl group instead of the $OCH_3$ group. This reaction is carried out in a manner known per se by the action of mineral acids, such as hydriodic acid, or Lewis acids, such as aluminum chloride or boron tribromide, in suitable solvents, such as, for example, methylene chloride or chloroform.

In the event that Z denotes a protective group of the general formula III, the anisoles XII can be prepared from anisoles XIII by a sequence of standard methods, as follows:

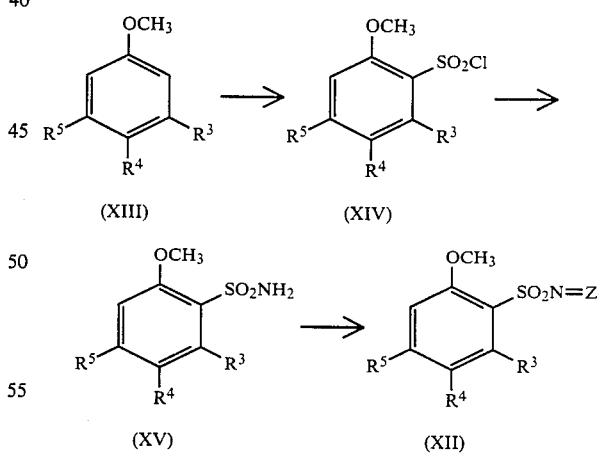

The action of chlorosulfonic acid on the anisoles XIII gives the sulfochlorides XIV in a manner known per se (Houben-Weyl, Methoden der organischen Chemie [Methods of Organic Chemistry], Volume X, page 563 et seq., G. Thieme Verlag Stuttgart 1955), and the sulfonamides XV are obtained from the latter by the action of ammonia. These sulfonamides are converted into the protected sulfonamides XII in a manner analogous to that described in German Offenlegungsschrift 2,658,766 or 2,461,601 by the action of substituted formamides, for example dimethylformamide, in the presence of a reagent which promotes the elimination of water, such as thionyl chloride or phosphorus oxychloride. It is also possible to employ, instead of the formamides, the acetals thereof, such as, for example, dimethylformamide dimethylacetal; in this case the reaction then takes place, in most cases, without any condensation agent being added.

In the event that Z represents the two radicals $R^1$ and $R^2$, the latter having the meanings mentioned above, with the exception of that of hydrogen, the anisoles XII are prepared in a known manner from the sulfochlorides XIV and the amines of the formula X.

The anisoles XIII are prepared by standard methods (Organikum, VEB Deutscher Verlag der Wissenschaften; Berlin 1971, page 222) from phenols.

Compounds of the formula I in which both $R^7$ and $R^6$ are alkyl radicals or are attached to one another to form a ring, as defined initially, are advantageously prepared in accordance with process variant b by subjecting the phenols II to a reaction of the Mannich type with amines of the general formula VI. Formaldehyde is in this case preferably employed in the form of an aqueous solution, but it is also possible to use any other customary variant of the Mannich reaction, such as, for example, the use of paraformaldehyde. The solvent can also be varied within wide limits, particularly suitable solvents are alkanols, such as, for instance, methanol or ethanol. The reaction is carried out within a temperature range from 40° to 150° C., but preferably within a range from 60° to 100° C. The reaction time depends decisively on the temperature; the reactions are generally complete after a few hours. The products are preferably isolated by removing the solvent and excess reagents by evaporation. If phenols II in which Z denotes the sulfonamide protective group mentioned above have been employed, the next stage is a hydrolysis as described under process variant a. In most cases the products are obtained in the form of highly viscous oils which can either be purified by crystallization from a suitable solvent or converted into a crystalline acid addition salt.

If the compounds of the formula I are prepared by process variant c, the elimination of the protective group Y' from the compounds of the formula XI is carried out under the same conditions as those which have already been indicated for the saponification of compounds of the formula V under process variant a.

The sulfonamides XI are prepared by standard methods from the sulfochlorides IX and the amines X. In general, it is advisable to add an acid acceptor, such as, for example, a weak organic base, such as, for instance, triethylamine or pyridine; it is often advantageous to add a second equivalent of the amine X in order to absorb the hydrochloric acid liberated in this reaction. The solvents used are any solvent which is inert towards the reactants, such as, for example, ketones, esters or ethers; it has proved particularly advantageous to add the sulfochloride IX, either dissolved or in solid form, slowly and in portions to the amine X, dissolved in a ketone, such as acetone. In this way it is possible to avoid polymeric by-products, which are readily formed from the sulfochloride IX under conditions of base catalysis, since there is always a large excess of amine X present. For this reason the method which would otherwise be more customary, of initially taking a sulfochloride and adding the amine, proceeds less advantageously.

The reaction temperature can be between 0° and 150° C. In general, it is advisable to maintain the temperature within the range from 20° to 50° C. Since under certain circumstances the reaction takes place exothermically, it can be advantageous to cool the reaction mixture.

In general, the reaction products are isolated in a crystalline form by removing the solvent by evaporation or by adding a non-solvent, such as, for instance, water. In most cases a further purification is required; in many cases recrystallization from an organic solvent is adequate, advantageous solvents being alkanols, such as n-butanol, isopropanol or ethanol.

The sulfochlorides IX are prepared from the phenols VII in a manner known per se. In this process it is not absolutely necessary for the phenolic group also to be protected; the free phenols can also be employed advantageously ($Y^2$=H in the formula VII). The reaction is achieved by the action of a sulfonating agent, such as sulfuric acid or chlorosulfonic acid, followed by the action of a chlorinating agent, such as, for instance, sulfuryl chloride, thionyl chloride or chlorosulfonic acid. It is preferable to use a process in which 2 or more equivalents of chlorosulfonic acid are allowed to act on the phenol VII. The solvents customary for chlorosulfonation reactions are used, such as, for instance, chlorinated hydrocarbons (for example chloroform or methylene chloride), or, which is particularly advantageous, the reaction is carried out without any solvent or excess chlorinating agent, such as the chlorosulfonic acid, is used as the solvent. The reaction temperature can be varied within wide limits, for example between −20° and +50° C., a temperature range from 0° to +20° C. being preferable.

The reaction product is in most cases isolated by adding a non-solvent, such as ice water, which at the same time destroys excess chlorinating agent and/or chlorosulfonating agent. A further purification is in most cases not necessary or, if required, can be effected easily by recrystallization, for example from non-polar organic solvents, such as toluene.

The phenols VII are prepared by acylating salicylamines XVI with suitable acylating agents

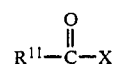

in which $R^{11}$ has the meaning mentioned above and X represents a leaving group customary for reactions of this type, such as, for instance, halogen.

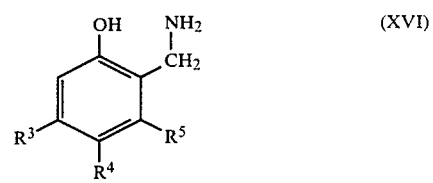

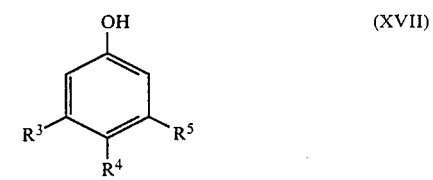

The salicylamines XVI can be prepared by standard methods.

The phenols VIII (in which $Y^2=H$) can also be prepared direct from phenols XVII by the Tscherniac-Einhorn reaction, using the hydroxymethylcarboxamides of the formula IV.

The compounds of the formula I which have been prepared by the various process variants are obtained in the form either of free bases or of acid addition salts. In order to prepare the free base from an acid addition salt it is necessary to treat the salt with at least one equivalent of a base. Both organic and inorganic bases are suitable in this regard, for example triethylamine, tetraethylammonium hydroxide or piperidine or lithium hydroxide, sodium hydroxide, potassium hydroxide, sodium bicarbonate, sodium carbonate and the like. In this reaction it is advantageous to employ the acid addition salt in a dissolved form, for example in alkanols, such as methanol or ethanol, or, which has proved particularly advantageous, in the form of aqueous solutions in which the addition of an inorganic base, such as, for instance, sodium hydroxide, results in precipitation of the crystalline free base I.

Conversely, acid addition products containing a desired acid HA are prepared by treating solutions of the free base I with at least one equivalent of the acid HA; either alcoholic solutions, such as, for instance, a methanolic solution, or an aqueous solution are preferred. The acid addition salt crystallizes either forthwith or after the removal of the solvent, or in some cases after recrystallization from a suitable solvent.

The following acids HA are suitable for pharmaceutically preferred acid addition salts: organic acids, such as tartaric acid, malic acid, lactic acid, acetic acid, citric acid, methanesulfonic acid, benzenesulfonic acid and others, or inorganic acids, such as hydrochloric, hydrobromic or hydriodic acid, sulfuric acid, nitric acid, phosphoric acid, sulfamic acid and the like.

The hydrohalides of amines I, which are readily soluble in water, such as, for example, the hydrochloride, are particularly preferred.

In addition to the compounds described in the illustrative embodiments, the compounds of the general formula I which are listed in the following table can also be obtained in accordance with the invention:

| $R_1$ | $R_2$ | $R_3$ | $R_4$ | $R_5$ | $R_6$ | $R_7$ |
|---|---|---|---|---|---|---|
| H | H | H | t-Amyl | H | H | H |
| H | H | H | n-Pentyl | H | H | H |
| H | H | H | 1-Methyl-cyclohexyl | H | H | H |
| H | H | H | cyclo-$C_6H_{11}$ | H | H | H |
| H | H | H | cyclo-$C_7H_{13}$ | H | H | H |
| H | H | H | 1,1-Dimethylbutyl | H | H | H |
| H | H | H | 1,1-Diethylpropyl | H | H | H |
| H | H | $OCH_3$ | Cl | $OCH_3$ | H | H |
| H | H | $OC_2H_5$ | Cl | $OC_2H_5$ | H | H |
| H | H | $OCH_3$ | t-Butyl | $OCH_3$ | H | H |
| H | H | $CH_3$ | $CH_3$ | $CH_3$ | H | H |
| H | H | $CH_3$ | t-Butyl | $CH_3$ | H | H |
| H | H | $CH_3$ | $C_2H_5$ | $CH_3$ | H | H |
| H | H | $C_2H_5$ | $CH_3$ | $C_2H_5$ | H | H |
| $C_3H_7$ | $C_3H_7$ | H | t-Butyl | H | H | H |
| $C_4H_9$ | $C_4H_9$ | H | t-Butyl | H | H | H |
| H | H | $C_2H_5$ | Cl | $C_2H_5$ | H | H |
| H | $C_3H_7$ | H | t-Butyl | H | H | H |
| —[$CH_2$]$_5$— | | H | t-Butyl | H | H | H |
| H | H | H | Cl | F | H | H |
| H | H | H | Cl | Cl | H | H |
| H | H | H | Cl | $CH_3$ | H | H |
| H | H | H | Cl | $OCH_3$ | H | H |
| H | H | F | Cl | H | H | H |
| H | H | Cl | Cl | H | H | H |
| H | H | $CH_3$ | Cl | H | H | H |
| H | H | $OCH_3$ | Cl | H | H | H |
| H | H | —($CH_2$)$_4$— | | H | H | H |
| H | H | H | —($CH_2$)$_4$— | | H | H |

The compounds, according to the invention, of the formula I and pharmacutically acceptable salts thereof are diuretics and salidiuretics which can be employed as pharmaceutical products in human and veterinary medicine. They are administered in daily doses of 0.5 to 300 mg, preferably 5-100 mg and especially 5-50 mg, calculated for an adult of normal weight, in capsules, dragees, tablets or solutions containing various additives enterally, for example orally by means of a probe or the like, or parenterally (injection into the vascular system, for example intravenously, or intramuscular or subcutaneous injection and the like). They are suitable for the treatment of hypertension as well as for the treatment of edema diseases, such as cardiac, renal or hepatic edemas, and other symptoms due to impairment of the water and electrolyte balance.

The compounds can be used on their own or in combination with other substances having a salidiuretic action, even whose having a different mode of action. The following should be mentioned particularly: spironolactone, triamterene, amiloride and other $K^+$-retaining compounds. However, other purely hypotensive compounds are also suitable as possible partners for combination, for example hydralazine, clonidine, reserpine and, particularly, also beta-blocking substances, such as, for instance, metoprolol or penbutolol.

EXAMPLE 1

2-Aminomethyl-4-(1,1-dimethylethyl)-6-sulfamoyl-phenol hydrochloride (a) 3-(1,1-Dimethylethyl)-6-methoxybenzenesulfonyl chloride 12.3 g (0.075 mole) of 4-(1,1-dimethylethyl)anisole, dissolved in 30 ml of methylene chloride, are added dropwise, while cooling with ice, to 16.5 ml of chlorosulfonic acid, dissolved in 20 ml of methylene chloride. The mixture is stirred for 40 minutes and is then poured into ice water. The organic phase is separated off, washed with water, dried with $MgSO_4$ and concentrated.

Recrystallization from toluene/petroleum ether gives crystals of melting point 75°–77° C.

(b)
3-(1,1-Dimethylethyl)-6-methoxybenzenesulfonamide 25.3 g (0.1 mole) of 3-(1,1-dimethylethyl)-6-methoxybenzenesulfonyl chloride are dissolved in a little acetone and the solution is added dropwise slowly, at room temperature, to 100 ml of concentrated ammonia solution. The mixture is stirred for 30 minutes at room temperature and poured into ice water. After acidification with concentrated hydrochloric acid the product is filtered off with suction. It is recrystallized from isopropanol.

White crystals of melting point 156°–158° C.

(c)
4-(1,1-Dimethylethyl)-2-dimethylaminomethyleneaminosulfonylanisole 4.68 g (0.02 mole) of 3-(1,1-dimethylethyl)-6-methoxybenzenesulfonamide are dissolved in 50 ml of dimethylformamide, and 2.5 g (0.022 mole) of dimethylformamide dimethylacetal are added. The mixture is left to stand for 30 minutes at room temperature and is poured into ice water and the product is filtered off with suction.

White crystals of melting point 134°–136° C.

(d)
4-(1,1-Dimethylethyl)-2-dimethylaminomethyleneaminosulfonylphenol 2.98 g (0.01 mole) of 4-(1,1-dimethylethyl-2-dimethylaminomethyleneaminosulfonylanisole are dissolved in 30 ml of methylene chloride, and 2.75 g (0.011 mole) of boron tribromide are added. The mixture is stirred for 45 minutes at room temperature and excess boron tribromide is destroyed cautiously by adding methanol. The mixture of solvents is removed in vacuo and the residue is triturated with water. The product is obtained in the form of slightly yellowish crystals. It is recrystallized from isopropanol.

Melting point 162°–164° C.

(e)
2-Chloro-N-[5-(1,1-dimethylethyl)-3-dimethylaminomethyleneaminosulfonyl-2-hydroxybenzyl]-acetamide 3 g (0.01 mole) of 4-(1,1-dimethylethyl)-2-dimethylaminomethyleneaminosulfonylphenol are dissolved in 30 ml of sulfuric acid, and 1.1 g (0.009 mole) of 2-chloro-N-hydroxymethylacetamide are added. The mixture is stirred for 30 minutes at room temperature and poured into ice water. The product is filtered off with suction and recrystallized from methanol.

White crystals of melting point 166°–169° C.

(f)
2-Aminomethyl-4-(1,1-dimethylethyl)-6-sulfamoylphenol hydrochloride 3 g (0.008 mole) of 2-chloro-N-[5-(1,1-dimethylethyl)-3-dimethylaminomethyleneaminosulfonyl-2-hydroxybenzyl]-acetamide in a mixture of 30 ml of ethanol and 3 ml of concentrated hydrochloric acid are heated under reflux for 2 hours. The solvent is removed in vacuo and the residue is crystallized from methanol/ether.

White crystals of melting point 226°–228° C. (decomposition).

EXAMPLE 2

2-Aminomethyl-4-isopropyl-6-sulfamoylphenol hydrochloride

The compound is prepared analogously to the sequence of reactions described in Example 1, but using 4-isopropylanisole as the starting material. The intermediate products and the end product have the following melting points:

(a) 3-Isopropyl-6-methoxybenzenesulfonyl chloride: melting point 60°–62° C.
(b) 3-Isopropyl-6-methoxybenzenesulfonamide: melting point 167°–169° C.
(c) 2-Dimethylaminomethyleneaminosulfonyl-4-isopropylanisole, melting point 124°–125° C.
(d) 2-Dimethylaminomethyleneaminosulfonyl-4-isopropylphenol, melting point 97°–99° C.
(e) 2-Chloro-N-(3-dimethylaminomethyleneaminosulfonyl-2-hydroxy-5-isopropylbenzyl)-acetamide, melting point 124°–126° C.
(f) 2-Aminomethyl-4-isopropyl-6-sulfamoylphenol hydrochloride, melting point 243°–246° C. (decomposition)

EXAMPLE 3

2-Aminomethyl-4-propyl-6-sulfamoylphenol hydrochloride

The compound is prepared analogously to the sequence of reactions described in Example 1, but using 4-propylanisole as the starting material. The intermediate products and the end product have the following melting points:

(a) 2-Methoxy-2-propylbenzenesulfonyl chloride, oil
(b) 2-Methoxy-5-propylbenzenesulfonamide, melting point 132°–134° C.
(c) 2-Dimethylaminomethyleneaminosulfonyl-4-propylanisole, melting point 118°–121° C.
(d) 2-Dimethylaminomethyleneaminosulfonyl-4-propylphenol, melting point 88°–90° C.
(e) 2-Chloro-N-(3-dimethylaminomethyleneaminosulfonyl-2-hydroxy-5-propylbenzyl)-acetamide, melting point 111 114° C.
(f) 2-Aminomethyl-4-propyl-6-sulfamoylphenol hydrochloride, melting point 232°–235° C. (decomposition).

EXAMPLE 4

2-Aminomethyl-4-methyl-6-sulfamoylphenol hydrochloride

The compound is prepared analogously to the sequence of reactions described in Example 1, but using 4-methylanisole as the starting material. The intermediate products and the end product have the following melting points:

(a) 2-Methoxy-5-methylbenzenesulfonyl chloride, melting point 86°–88° C.
(b) 2-Methoxy-5-methylbenzenesulfonamide, melting point 185°–188° C.
(c) 2-Dimethylaminomethyleneaminosulfonyl-4-methylanisole, melting point 146°–148° C.
(d) 2-Dimethylaminomethyleneaminosulfonyl-4-methylphenol, melting point 150°–152° C.
(e) 2-Chloro-N-(3-dimethylaminomethyleneaminosulfonyl-2-hydroxy-5-methylbenzyl)-acetamide, melting point 176°–178° C.
(f) 2-Aminomethyl-4-methyl-6-sulfamoylphenol hydrochloride, melting point 230°–233° C. (decomposition).

EXAMPLE 5

2-Aminomethyl-4-chloro-6-sulfamoylphenol hydrochloride

The compound is prepared analogously to the sequence of reactions described in Example 1, but using 4-chloroanisole as the starting material. The intermediate products and the end product have the following melting points:

(a) 3-Chloro-6-methoxybenzenesulfonyl chloride, melting point 102°–103° C.

(b) 3-Chloro-6-methoxybenzenesulfonamide, melting point 147°–149° C.
(c) 2-Dimethylaminomethyleneaminosulfonyl-4-chloroanisole, melting point 171°–174° C.
(d) 2-Dimethylaminomethyleneaminosulfonyl-4-chlorophenol, melting point 159°–162° C.
(e) 2-Chloro-N-(3-dimethylaminomethyleneaminosulfonyl-5-chlorobenzyl)-acetamide, melting point 135°–140° C.
(f) 2-Aminomethyl-4-chloro-6-sulfamoylphenol hydrochloride, melting point 252°–255° C. (decomposition).

EXAMPLE 6

2-Aminomethyl-4-(1-methylpropyl)-6-sulfamoylphenol hydrochloride

The compound is prepared analogously to the sequence of reactions described in Example 1, but using 4-(1-methylpropyl)-anisole as the starting material. The intermediate products and the end product have the following melting points:
(a) 2-Methoxy-5-(1-methylpropyl)-benzenesulfonyl chloride, melting point: oil
(b) 2-Methoxy-5-(1-methylpropyl)-benzenesulfonamide, melting point 120°–122° C.
(c) 2-Dimethylaminomethyleneaminosulfonyl-4-(1-methylpropyl)-anisole, melting point 93°–95° C.
(d) 2-Dimethylaminomethyleneaminosulfonyl-4-(1-methylpropyl)-phenol, melting point 87°–91° C.
(e) 2-Chloro-N-[3-dimethylaminomethyleneaminosulfonyl-2-hydroxy-5-(1-methylpropyl)-benzyl]-acetamide, melting point 103°–105° C.
(f) 2-Aminomethyl-4-(1-methylpropyl)-6-sulfamoylphenol hydrochloride, melting point 218°–222° C. (decomposition).

EXAMPLE 7

2-Aminomethyl-4-ethyl-6-sulfamoylphenol hydrochloride

The compound is prepared analogously to the sequence of reactions described in Example 1, but using 4-ethylanisole as the starting material. The intermediate products and the end product have the following melting points:
(a) 2-Methoxy-5-ethylbenzenesulfonyl chloride, melting point 58°–60° C.
(b) 2-Methoxy-5-ethylbenzenesulfonamide, melting point 162°–165° C.
(c) 2-Dimethylaminomethyleneaminosulfonyl-4-ethylanisole, melting point 140°–142° C.
(d) 2-Dimethylaminomethyleneaminosulfonyl-4-ethylphenol, melting point 100°–102° C.
(e) 2-Chloro-N-(3-dimethylaminomethyleneaminosulfonyl-2-hydroxy-5-ethylbenzyl)-acetamide, melting point 130°–133° C.
(f) 2-Aminomethyl-4-ethyl-6-sulfamoylphenol hydrochloride, melting point 234°–238° C. (decomposition).

EXAMPLE 8

2-Aminomethyl-4-chloro-3,5-dimethyl-6-sulfamoylphenol hydrochloride

The compound is prepared analogously to the sequence of reactions described in Example 1, but using 4-chloro-3,5-dimethylphenol as the starting material.

The intermediate products and the end product have the following melting points:
(a) 3-Chloro-2,4-dimethyl-6-methoxybenzenesulfonyl chloride, melting point 88°–90° C.
(b) 3-Chloro-2,4-dimethyl-6-methoxybenzenesulfonamide, melting point 208°–212° C.
(c) 2-Dimethylaminomethyleneaminosulfonyl-4-chloro-3,5-dimethylanisole, melting point 204°–206° C.
(d) 2-Dimethylaminomethyleneaminosulfonyl-4-chloro-3,5-dimethylphenol, melting point 142°–146° C.
(e) 2-Chloro-N-(3-dimethylaminomethyleneaminosulfonyl-5-chloro-4,6-dimethyl-2-hydroxybenzyl)-acetamide, melting point 130°–133° C.
(f) 2-Aminomethyl-4-chloro-3,5-dimethyl-6-sulfamoylphenol hydrochloride, melting point 256°–260° C. (decomposition).

EXAMPLE 9

1-Aminomethyl-3-sulfamoyl-5,6,7,8-tetrahydro-2-naphthol hydrochloride (a) 3-Chlorosulfonyl-5,6,7,8-tetrahydro-2-naphthol methyl ether 118 g (0.73 mole) of 5,6,7,8-tetrahydro-2-naphthol methyl ether are dissolved in 320 ml of methylene chloride, and 177 ml of chlorosulfonic acid in 160 ml of methylene chloride are added. The mixture is stirred for 10 minutes at 5° C. and is poured into ice water. The organic phase is separated off and dried with MgSO$_4$. The solvent is removed by evaporation and the residue is recrystallized from acetone/petroleum ether.

White crystals of melting point 103°–104° C.

(b) 3-Dimethylaminomethyleneaminosulfonyl-5,6,7,8-tetrahydro-2-naphthol methyl ether 32 g (0.013 mole) of 3-chlorosulfonyl-5,6,7,8-tetrahydro-2-naphthol methyl ether are dissolved in a little acetone, the solution is added dropwise to 100 ml of concentrated ammonia solution, and the mixture is left to stand for 30 minutes at room temperature. It is acidified with concentrated hydrochloric acid and extracted by shaking with ethyl acetate, and the extract is dried with MgSO$_4$ and concentrated. The residue is dissolved in 100 ml of dimethylformamide, and 24 g (0.2 mole) of dimethylformamide methylacetal are added to the solution. The mixture is stirred for 30 minutes at room temperature and poured into ice water and the product is filtered off with suction. Recrystallization from methanol gives crystals of melting point 210°–213° C.

(c) 3-Dimethylaminomethyleneaminosulfonyl-5,6,7,8-tetrahydro-2-naphthol

The ether is split analogously to Example 1 d.
White crystals of melting point 163°–164° C.

(d) 2-Chloro-N-(3-dimethylaminomethyleneaminosulfonyl-2-hydroxy-5,6,7,8-tetrahydronaphthylmethyl)-acetamide This compound is prepared analogously to Example 1 e.
Melting point 99°–101° C.

(f)
1-Aminomethyl-3-sulfamoyl-5,6,7,8-tetrahydro-2-naphthol hydrochloride

This compound is prepared analogously to Example 1 f. Melting point 240°–244° C. (decomposition).

EXAMPLE 10

2-Aminomethyl-4-cyclopentyl-6-sulfamoylphenol hydrochloride (a)
1-Acetamidomezhyl-2-acetoxy-4-cyclopentylbenzene 15 g (0.07 mole) of 2-aminomethyl-4-cyclopentylphenol hydrochloride are suspended in 150 ml of dioxane. 12 g (0.15 mole) of pyridine and 11.8 g (0.15 mole) of acetyl chloride are added dropwise, and the mixture is stirred for 2.5 hours at 90° C. The mixture is poured into ice water, and the product is filtered off with suction and dried in air.
White crystals of melting point 203°–205° C.

(b)
3-Acetamidomethyl-4-cyclopentyl-2-hydroxybenzenesulfonamide 11 g (0.04 mole) of 1-acetamidomethyl-2-acetoxy-4-cyclopentylbenzene are introduced at room temperature into 100 ml of chlorosulfonic acid. The mixture is stirred for 15 minutes at room temperature and is poured into ice water. This mixture is filtered with suction, the residue is dissolved in methyl acetate, and the solution is dried with $MgSO_4$ and chromatographed over silica gel, using ethyl acetate as the eluting agent. The solvent is removed in vacuo, the residue is dissolved in a little acetone and the solution is added dropwise to 100 ml of concentrated ammonia solution. The mixture is stirred for 30 minutes at room temperature and acidified with concentrated hydrochloric acid to pH 2. The product is filtered off with suction and rinsed with plenty of water, and the resulting mash of crystals is boiled with n-butanol.
White crystals of melting point 243°–246° C.

(c) 2-Aminomethyl-4-cyclopentyl-6-sulfamoylphenol hydrochloride 3.4 g (0.012 mole) of 3-acetamidomethyl-2-acetoxy-2-hydroxybenzenesulfonamide in a mixture of 30 ml of ethanol and 10 ml of concentrated hydrochloric acid are heated under reflux for 8 hours. After removing the solvent, the residue is recrystallized from methanol/ether.
White crystals of melting point 243°–246° C.

EXAMPLE 11

2-Aminomethyl-4-(1,1-dimethylethyl)-6-methylsulfamoylphenol hydrochloride (a) 2-Acetamidomethyl-4-(1,1-dimethylethyl)-phenol 43 g (0.2 mole) of 2-aminomethyl-4-(1,1-dimethylethyl)-phenol hydrochloride are suspended in 400 ml of 1,4-dioxane, and 40 ml of pyridine are added. 40 ml (0.55 mole) of acetyl chloride are added dropwise while stirring and cooling with ice. The mixture is then stirred for 2.5 hours at 90° and poured into ice water, and the precipitate which has crystallized out is filtered off with suction.
White crystals of melting point 99°–102° C.

(b)
2-Acetamidomethyl-6-chlorosulfonyl-4-(1,1-dimethylethyl)-phenol 15.5 g (0.059 mole) of 2-acetamidomethyl-4-(1,1-dimethylethyl)-phenol are introduced at room temperature into 100 ml of chlorosulfonic acid. Stirring is continued for a further 15 minutes and the solution is stirred into ice water. The precipitate is filtered off with suction and recrystallized from toluene.
Colorless crystals of melting point 145°–147° C.

(c)
2-Acetamidomethyl-4-(1,1-dimethylethyl)-6-methylsulfamoylphenol 9 g (0.028 mole) of 2-acetamidomethyl-6-chlorosulfonyl-4-(1,1-dimethylethyl)-phenol are dissolved in 100 ml of acetone, and 4.9 ml (0.056 mole) of 40% strength aqueous methylamine solution are added dropwise, while cooling with ice. The mixture is stirred for 30 minutes at room temperature and poured into ice water. Recrystallization from n-propanol gives white crystals of melting point 173°–174° C.

(d)
2-Aminomethyl-4-(1,1-dimethylethyl)-6-methylsulfamoylphenol hydrochloride 4.9 g (0.016 mole) of 6-acetamidomethyl-4-(1,1-dimethylethyl)-2-methylsulfamoylphenol in a mixture of 30 ml of ethanol and 10 ml of concentrated hydrochloric acid are heated under reflux for 8 hours. Evaporation and recrystallization from methanol/ether gives white crystals of melting point 238°–240° C.

EXAMPLE 12

2-Aminomethyl-4-(1,1-dimethylethyl)-6-dimethylsulfamoylphenol hydrochloride

This compound is prepared analogously to Examples 11 c and 11 d from 2-acetamidomethyl-6-chlorosulfonyl-4-(1,1-dimethylethyl)-phenol and dimethylamine.
White crystals of melting point 129°–131° C.

EXAMPLE 13

2-Aminomethyl-6-diethylsulfamoyl-4-(1,1-dimethylethyl)-phenol hydrochloride

This compound is prepared analagously to Examples 11 c and 11 d from 2-acetamidomethyl-6-chlorosulfonyl-4-(1,1-dimethylethyl)-phenol and diethylamine.
Colorless needles of melting point 125°–127° C.

EXAMPLE 14

2-Aminomethyl-4-(1,1-dimethylethyl)-6-ethylsulfamoylphenol hydrochloride

This compound is prepared analogously to Examples 11 c and 11 d from 2-acetamidomethyl-6-chlorosulfonyl-4-(1,1-dimethylethyl)-phenol and ethylamine.
White crystals of melting point 102°–105° C.

EXAMPLE 15

2-Aminomethyl-6-butylsulfamoyl-4-(1,1-dimethylethyl)-phenol hydrochloride

This compound is prepared analogously to Examples 11 c and 11 d from 2-acetamidomethyl-6-chlorosulfonyl-4-(1,1-dimethylethyl)-phenol and butylamine.
White crystals of melting point 81°–84° C.

EXAMPLE 16

2-Aminomethyl-4-(1,1-dimethylethyl)-6-(1-pyrrolidinylsulfonyl)-phenol hydrochloride This compound is prepared analogously to Examples 11 c and 11 d from 2-acetamidomethyl-6-chlorosulfonyl-4-(1,1-dimethylethyl)-phenol and pyrrolidine.
Colorless crystals of melting point 168°–172° C.

EXAMPLE 17

4-Aminomethyl-5-hydroxy-6-sulfamoylindane hydrochloride (a) 6-Chlorosulfonyl-5-methoxyindane 50 g (0.34 mole) of 5-methoxyindane are reacted with 75 ml of chlorosulfonic acid analogously to Example 1 a to give 6-chlorosulfonyl-5-methoxyindane.
White crystals of melting point 75°–77° C.

(b) 5-Methoxy-6-sulfamoylindane

This compound is prepared analogously to Example 1 b from 6-chlorosulfonyl-5-methoxyindane.
White crystals of melting point 91°–92° C.

(c) 5-Methoxy-6-dimethylaminomethyleneaminosulfonylindane

This compound is prepared analogously to Example 1 c from 5-methoxy-6-sulfamoylindane and dimethylformamide dimethylacetal.
White crystals of melting point 238°–241° C.

(d) 5-Hydroxy-6-dimethylaminomethyleneaminosulfonylindane

This compound is prepared analogously to Example 1 d from 5-methoxy-6-dimethylaminomethyleneaminosulfonylindane and boron tribromide.
White crystals of melting point 180°–182° C.

(e) 4-(N-Chloroacetylaminomethyl)-5-hydroxy-6-dimethylaminomethyleneaminosulfonylindane This compound is prepared analogously to Example 1 e from 5-hydroxy-6-dimethylaminomethyleneaminosulfonylindane.
White crystals of melting point 156°–158° C.

(f) 4-Aminomethyl-5-hydroxy-6-sulfamoylindane hydrochloride

This compound is prepared analogously to Example 1 f from 4-(N-chloroacetylaminomethyl)-5-hydroxy-6-dimethylaminomethyleneaminosulfonylindane.
White crystals of melting point 256°–258° C. (decomposition).

EXAMPLE 18

6-Aminomethyl-5-hydroxy-4-sulfamoylindane hydrochloride (a) 6-(N-Chloroacetylaminomethyl)-5-hydroxyindane 134 g (1 mole) of 5-hydroxyindane and 100 g (0.81 mole) of 2-chloro-N-hydroxymethylacetamide are suspended in 300 ml of glacial acetic acid, and 10 ml of concentrated sulfuric acid are added. The mixture is stirred for 30 minutes at room temperature and is poured into ice water. The product is filtered off with suction and recrystallized from methanol.
Colorless crystals of melting point 158°–161° C.

(b) 6-(N-Chloroacetylaminomethyl)-5-hydroxy-4-chlorosulfonylindane 70 g (0.29 mole) of 6-(N-chloroacetylaminomethyl)-5-hydroxyindane are dissolved in 150 ml of chlorosulfonic acid, and the mixture is stirred for approx. 30 minutes at room temperature. The mixture is poured into ice water and the product is filtered off with suction. The initially crystalline material becomes oily after a little time and is employed in the next stage in this form without further purification.

(c) 6-(N-Chloroacetylaminomethyl)-5-hydroxy-4-sulfamoylindane 33.8 g (0.1 mole) of 6-(N-chloroacetylaminomethyl)-5-hydroxy-4-chlorosulfonylindane are dissolved in a little acetone, and the solution is added dropwise to 50 ml of concentrated ammonia solution. The mixture is stirred for 30 minutes at room temperature and is diluted with water. The precipitate which is deposited is filtered off with suction and dissolved in acetone, and the solution is filtered and stirred into water again.
White crystals of melting point 209°–212° C.

(d) 6-aminomethyl-5-hydroxy-4-sulfamoylindane hydrochloride

This compound is prepared analogously to Example 1 f from 6-(N-chloroacetylaminomethyl)-5-hydroxy-4-sulfamoylindane.
White crystals of melting point 245°–248° C. (decomposition).

EXAMPLE 19

2-Aminomethyl-4-(1-methylcyclohexyl)-6-sulfamoyl-phenol hydrochloride

This compound was prepared analogously to the sequence of reactions described in Example 1, but using 4-(1-methylcyclohexyl)-anisole as the starting material. The intermediate products and the end product had the following melting points:

(a) 2-Methoxy-5-(1-methylcyclohexyl)-benzenesulfonyl chloride, melting point: oil (b) 2-Methoxy-5-(1-methylcyclohexyl)-benzenesulfonamide, melting point 148°–151° C.

(c) 2-Dimethylaminomethyleneaminosulfonyl-4-(1-methylcyclohexyl)-anisole, melting point 78°–80° C.

(d) 2-Dimethylaminomethyleneaminosulfonyl-4-(1-methylcyclohexyl)-phenol, melting point 120°–22° C.

(e) 2-Chloro-N-[3-dimethylaminomethyleneaminosulfonyl-2-hydroxy-5-(1-methylcyclohexyl)-benzyl]-acetamide, melting point 123°–25° C.

(f) 2-Aminomethyl-4-(1-methylcyclohexyl)-6-sulfamoylphenol hydrochloride, melting point 193°–197° C.

EXAMPLE 20

2-Aminomethyl-4-(1,1-dimethylethyl)-6-(o-chlorobenzyl)-aminosulfonylphenol hydrochloride This compound is prepared analogously to Examples 11c and 11 d from 2-acetamidomethyl-6-chlorosulfonyl-4-(1,1-dimethylethyl)-phenol and o-chlorobenzylamine.
Melting point 180°–183° C.

EXAMPLE 21

2-Aminomethyl-4-(1,1-dimethylethyl)-6-alkylaminosulfonylphenol hydrochloride Prepared analogously to Examples 11 c and 11d from an alkylamine and 2-acetamidomethyl-6-chlorosulfonyl-4-(1,1-dimethylethyl)-phenol.

Melting point 140°–143° C.

EXAMPLE 22

2-Dimethylaminomethyl-4-(1,1-dimethylethyl)-6-sulfamoylphenol hydrochloride 2 g (0.007 mole) of 2-dimethylaminomethyleneaminosulfonyl-4-(1,1-dimethylethyl)-phenol are dissolved in 11 ml of ethanol, 3.7 ml of 35% strength aqueous formaldehyde solution and 4.7 ml of 40% strength dimethylamine solution in water are added, and the mixture is boiled undeF reflux for 1 hour. The solution is concentrated to dryness, the residue is taken up in 2 N hydrochloric acid and the solution is extracted several times with ethyl acetate. The aqueous phase is concentrated again, the residue is dissolved in ethanol and a little concentrated hydrochloric acid, and the solution is boiled under reflux for approx. 20 minutes and then concentrated until crystallization starts.

White crystals of melting point 210°–213° C.

EXAMPLE 23

2-Aminomethyl-4-(1,1-dimethylpropyl)-6-sulfamoylphenol hydrochloride

This compound was prepared analogously to the sequence of reactions described in Example 1, but using 4-(1,1-dimethylpropyl)-anisole as the starting material. The intermediate products and the end product had the following melting points:

(a) 2-Methoxy-5-(1,1-dimethylpropyl)-benzenesulfonyl chloride, oil
(b) 2-Methoxy-5-(1,1-dimethylpropyl)-benzenesulfonamide, melting point 117°–119° C.
(c) 2-Dimethylaminomethyleneaminosulfonyl-4-(1,1-dimethylpropyl)-anisole, melting point 109°–111° C.
(d) 2-Dimethylaminomethyleneaminosulfonyl-4-(1,1-dimethylpropyl)-phenol, melting point 150°–152° C.
(e) 2-Chloro-N-[3-dimethylaminomethyleneaminosulfonyl-2-hydroxy-5-(1,1-dimethylpropyl)-benzyl]-acetamide, melting point 127°–129° C.
(f) 2-Aminomethyl-4-(1,1-dimethylpropyl)-6-sulfamoylphenol hydrochloride, melting point 180°–182° C.

We claim:

1. A compound of formula II

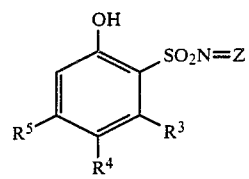

in which $R^3$ and $R^5$ are identical or different and denote hydrogen, halogen, alkyl having 1 or 2 carbon atoms or alkoxy having 1 or 2 carbon atoms, $R^4$ denotes halogen, alkyl having 1 to 12 carbon atoms or cycloalkyl having 3 to 12 carbon atoms and up to 8 ring members, or taken together either $R^3$ and $R^4$ or $R^4$ and $R^5$ form a —(CH$_2$)$_m$— chain in which m is 3 to 6 and which is unsubstituted or substituted by 1 or 2 methyl groups and z represents (a) $R^1$ and $R^2$, wherein $R^1$ and $R^2$ are identical or different and represent alkyl having 1 to 4 carbon atoms, alkenyl having 2 to 4 carbon atoms, alkynyl having 2 to 4 carbon atoms, or benzyl which is unsubstituted or substituted by methyl, methoxy, or halogen, or (b) a sulfonamide protecting group of the formula III

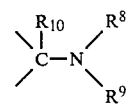

in which the radical $R^{10}$ denotes hydrogen or alkyl having 1 to 4 carbon atoms and $R^8$ and $R^9$ denote alkyl having 1 to 4 carbon atoms.

* * * * *